US 8,552,005 B2

(12) United States Patent
Ivashchenko et al.

(10) Patent No.: US 8,552,005 B2
(45) Date of Patent: Oct. 8, 2013

(54) (EN) 3-SULFONYL-PYRAZOLO[1,5-A] PYRIMIDINES / ANTAGONISTS OF SEROTONIN 5-HT$_6$ RECEPTORS, METHODS FOR THE PRODUCTION AND THE USE THEREOF

(75) Inventors: Andrey Alexandrovich Ivashchenko, Moscow (RU); Alexander Vasilievich Ivashchenko, Encinitas, CA (US); Nikolay Filippovich Savchuk, Rancho Santa Fe, CA (US)

(73) Assignee: Avincuro Pharmaceuticals, Inc., San Diego, CA (US)

( * ) Notice: Subject to any disclaimer, the term of this patent is extended or adjusted under 35 U.S.C. 154(b) by 320 days.

(21) Appl. No.: 12/812,728

(22) PCT Filed: Jan. 23, 2009

(86) PCT No.: PCT/IB2009/050270
§ 371 (c)(1),
(2), (4) Date: Sep. 13, 2010

(87) PCT Pub. No.: WO2009/093206
PCT Pub. Date: Jul. 30, 2009

(65) Prior Publication Data
US 2010/0331347 A1 Dec. 30, 2010

(30) Foreign Application Priority Data
Jan. 24, 2008 (RU) .............................. 2008102154

(51) Int. Cl.
| A01N 43/90 | (2006.01) |
| A01N 43/00 | (2006.01) |
| A61K 31/519 | (2006.01) |
| A61K 31/33 | (2006.01) |
| C07D 487/00 | (2006.01) |

(52) U.S. Cl.
USPC .......................... 514/259.3; 514/183; 544/281

(58) Field of Classification Search
USPC .................. 514/259.3, 183; 544/281
See application file for complete search history.

(56) References Cited

FOREIGN PATENT DOCUMENTS

| EP | 0941994 | 3/1999 |
| WO | WO97/11075 | 3/1997 |
| WO | WO03/057674 | 7/2003 |
| WO | WO 2007046548 A1 * | 4/2007 |

OTHER PUBLICATIONS

Vippagunta et al. Advanced Drug Delivery Reviews, 2001, vol. 48, pp. 3-26.*
Slivchuk S.R. et al.: A convenient approach to the synthesis of 3-(arylsulfonyl) pyrazol [1,5-a] pyrimidines and their condensed analogs. Ukraine Zhurnal Organichonoi Ta Farmatsevtichnoi Khimii vol. 4, No. 3, 2006, pp. 62-68.
Kirkpatrick We et al.: 3-Halo-5,7-Dimethylpyrazolo[1,5-A] Pyrimidines, A Nonbenzodiazepinoid Class of Antianxiety Agents Devoid of Potentiation of Central Nervous System Depressant Effects of Ethanol or Barbiturates. Journal of Medicinal Chemistry, ACS, US, vol. 20, No. 3, Mar. 1, 1977, pp. 386-393.
Holenz J.; Pauwels P.J.; Diaz J.L.; Merce R.; Codony X.; Buschmann H.: Medicinal chemistry strategies to 5-HT6 receptor ligands as potential cognitive enhancers and antiobesity agents. Drug Disc Today. vol. 11, 2006, pp. 283-299.
Gerard C.; Martres M.-P.; Lefevre K; Miquel M.-C.; Verge D.; Lanfumey L.; Doucet E., Hamon M.; EL Mestikavvy S.: Immunolocalisation of serotonin 5-HT6 receptor-like material in the rat central nervous system. Brain Research vol. 746, 1997, pp. 207-219.
Dawson L.A.; Nguyen H.Q.; Li P.: The 5-HT(6) receptor antagonist SB-271046 selectively enhances excitatory neurotransmission in the rat frontal cortex and hippocampus. Neuropsychopharmacology vol. 25, 2001, pp. 662-668.
Foley A.G.; Murphy K.J.; Hirst W.D.; Gallagher H.C.; Hagan J.J.; Upton N.; Walsh F.S.; Regan C.M.: The 5-HT(6) receptor antagonist SB-271046 reverses scopolamine-disrupted consolidation of a passive avoidance task and ameliorates spatial task deficits in aged rats. Neuropsychopharmacology vol. 29, 2004, pp. 93-100.
Rieivier C.; Borroni E; Levet-Trafit B.; Martin J.R.; Poli S.; Porter R.H.; Bos M.: Influence of the 5-HT6 receptor on acetylcholine release in the cortex: pharmacological characterization of 4-(2-bromo-6-pyrrolidin-1-ylpyridine-4-sulfonyl)phenylamine, a potent and selective 5-HT6 receptor antagonist. J Med. Chem. vol. 46, 2003, pp. 1273-1276.
King M.V.; Woolley M.L.; Topham I.A.; Sleight A.J.; Marsden C.A.: Fone K.C. 5-HT6 receptor antagonists reverse delay-dependent deficits in novel object discrimination by enhancing consolidation an effect sensitive to NMDA receptor antagonism. Neuropharmacology vol. 47, 2004, pp. 195-204.

(Continued)

Primary Examiner — Samira Jean-Louis

(57) ABSTRACT

The present invention relates to novel substituted 3-(arylsulfonyl)pyrazolo[1,5-a]pyrimidines of general formula 1 pharmaceutically acceptable salts and/or hydrates, to novel serotonin 5-HT$_6$ receptor antagonists, to novel drug substances, pharmaceutical compositions, medicaments and methods for their preparation and use for treatment and prophylaxis of pathological states and diseases of CNS, pathogenesis of which is associated with disturbance of serotonin 5-HT$_6$ receptor activation.
In compounds of general formula 1

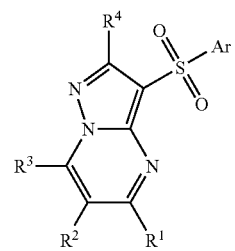

Ar represents optionally substituted aryl or heterocyclyl; $R^1$, $R^2$ and $R^3$ independently of each other represent hydrogen, $C_1$-$C_3$ alkyl or phenyl; $R^4$ represents hydrogen, optionally substituted $C_1$-$C_5$ alkyl, substituted hydroxyl group or substituted sulfanyl group.

10 Claims, No Drawings

(56) References Cited

OTHER PUBLICATIONS

Vicker S.P.; Dourish C.T.: Serotonin receptor ligands and the treatment of obesity. Curr. Opin. Investig. Drugs. vol. 5, 2004, pp. 377-388.

Davies S.L.: Drug discovery targets: 5-HT6 receptor. Drug Future vol. 30, 2005, pp. 479-495.

Woolley M.L.: 5-HT6 receptors. Curr. Drug Targets CNS Neurol. Disord. vol. 3, 2004, pp. 59-79.

Monsma FJ JR; Shen Y; Ward RP; Hamblin MW; Sibley DR: Cloning and expression of a novel serotonin receptor with high affinity far tricyclic psychotropic drugs. Mol Pharmacol. vol. 43, 1993, pp. 320-327.

\* cited by examiner

(EN) 3-SULFONYL-PYRAZOLO[1,5-A] PYRIMIDINES / ANTAGONISTS OF SEROTONIN 5-HT$_6$ RECEPTORS, METHODS FOR THE PRODUCTION AND THE USE THEREOF

FIELD OF THE INVENTION lkoxy, The invention relates to novel 3-(arylsulfonyl)pyrazolo[1,5-a]pyrimidines, to novel serotonin 5-HT$_6$ receptor antagonists, drug substances, pharmaceutical compositions, medicaments, methods for their preparation and use. More specifically, the invention relates to serotonin 5-HT$_6$ receptor antagonists—substituted 3-(sulfonyl)pyrazolo[1,5-a]pyrimidines, to drug substances and pharmaceutical compositions, comprising the said compounds as active ingredients, and to methods of treatment and prophylaxis of central nervous system (CNS) diseases, among them cognitive and neurodegenerative diseases. The origin of pharmacological action of novel drug substances is their ability to interact with serotonin 5-HT$_6$ receptors playing the key role in treatment of CNS diseases, in particular, Alzheimer's disease (AD), Huntington's disease, schizophrenia, other neurodegenerative diseases, cognitive disorders and obesity.

BACKGROUND OF THE INVENTION

Usefulness of selective antagonists of serotonin 5-HT$_6$ receptors for treating of CNS diseases, in particular, schizophrenia, AD and other neurodegenerative diseases and cognitive disorders was proved conclusively in clinical practice and is regarded to be very perspective in medicine of future [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299]. At mammals these receptors are localized exclusively in central nervous system (CNS), and mainly in the parts of brain responsible for training and memory [Ge'rard C., Martres M.-P., Lefe'vre K., Miguel M.-C., Verge' D., Lanfumey L., Doucet E., Hamon M., El Mestikawy S. Immuno-localisation of serotonin 5-HT$_6$ receptor-like material in the rat central nervous system. *Brain Research.* 1997; 746:207-219]. Besides, it was shown [Dawson L. A., Nguyen H. Q., Li P. The 5-HT(6) receptor antagonist SB-271046 selectively enhances excitatory neurotransmission in the rat frontal cortex and hippocampus. *Neuropsychopharmacology.* 2001; 25:662-668], that 5-HT$_6$ receptors are modulators of the whole number of neuromediator systems including cholinergic, noradrenergic, glutamatergic and dopaminergic. Taking into account the fundamental role of these systems in normal cognitive processes and their dysfunction at neurodegeneration, exclusive role of 5-HT$_6$ receptors in forming normal and "pathological" memory becomes obvious.

It was shown in a large number of nowadays publications that blocking of 5-HT$_6$ receptors leads to considerable enhancement of memory consolidation in various animal models of training-memorizing-reproduction [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. *Neuropsychopharmacology.* 2004; 29:93-100. Riemer C., Borroni E., Levet-Trafit B., Martin J. R., Poli S., Porter R. H., Bos M. Influence of the 5-HT6 receptor on acetylcholine release in the cortex: pharmacological characterization of 4-(2-bromo-6-pyrrolidin-1-ylpyridine-4-sulfonyl)phenylamine, a potent and selective 5-HT$_6$ receptor antagonist. *J. Med. Chem.* 2003; 46:1273-1276. King M. V., Woolley M. L., Topham I. A., Sleight A. J., Marsden C. A., Fone K. C. 5-HT6 receptor antagonists reverse delay-dependent deficits in novel object discrimination by enhancing consolidation an effect sensitive to NMDA receptor antagonism. *Neuropharmacology* 2004; 47:195-204]. It was also demonstrated that considerable enhancement of cognitive functions in aged rats in Morrison's water maze experiment took place under the action of 5-HT$_6$ receptor antagonists [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. *Neuropsychopharmacology* 2004; 29:93-100]. Recently more thorough understanding of 5-HT$_6$ receptor function in cognitive processes and more accurate conceptions concerning possible pharmacophoric properties of their antagonists were achieved. [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299]. This resulted in preparation of highly affine selective ligands ("molecular tools"), and afterwards clinical candidates. At present a number of 5-HT$_6$ receptor antagonists are at various phases of clinical investigation as potential ingredients for treatment of AD, Huntington's disease, schizophrenia (antipsychotic) and other neurodegenerative and cognitive diseases (Table 1) [http://integrity.prous.com].

TABLE 1

5-HT$_6$ receptor antagonists as drug candidates.

| Medicament | Clinical phase of testing | Developer | Therapeutic group |
|---|---|---|---|
| Dimebon ™ | Phase III | Medivation (USA) | Alzheimer's disease treatment |
| SGS-518 | Phase II | Lilly, Saegis | Cognitive diseases treatment |
| SB-742457 | Phase II | GlaxoSmithKline | Alzheimer's disease treatment; Antipsychotic |
| Dimebon* | Phase I/IIa | Medivation (USA) | Huntington's disease treatment |
| Dimebon* | Phase II | (Russia) | Schizophrenia |
| PRX-07034 | Phase I | Epix Pharm. | Obesity treatment; Antipsychotic; Cognitive diseases treatment |
| SB-737050A | Phase II | GlaxoSmithKline | Antipsychotic |
| BVT-74316 | Phase I | Biovitrum | Obesity treatment |
| SAM-315 | Phase I | Wyeth Pharm. | Alzheimer's disease treatment |
| SYN-114 | Phase I | Roche, Synosis Ther. | Cognitive diseases treatment |
| BGC-20-761 | Preclinical | BTG (London) | Antipsychotic; Cognitive diseases treatment |
| FMPO | Preclinical | Lilly | Antipsychotic |
| Dimebon ™ | Preclinical | (Russia) | Insult treatment |

Another attractive property of 5-HT$_6$ receptor antagonists is their ability to suppress appetite that can lead to preparation on their basis of essentially novel remedies for overweight lowering and obesity treatment. [Vicker S. P., Dourish C. T. Serotonin receptor ligands and the treatment of obesity. *Curr. Opin. Investig. Drugs.* 2004; 5:377-388]. This effect was confirmed in many investigations [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299. Davies S. L. Drug discovery targets: 5-HT$_6$ receptor. *Drug Future.* 2005; 30:479-495], its mechanism is based on suppression of γ-aminobutyric acid signaling by 5-HT$_6$ receptor antagonists and increasing of α-melanocyte-stimulating hormone emission, that, finally, results in lowering of food demand [Woolley M. L. 5-HT$_6$ receptors. *Curr. Drug Targets CNS Neurol. Disord.* 2004; 3:59-79]. Now two 5-HT$_6$ receptor antagonists are at the first phase of clinical testing as drug candidates for obesity treatment (Table 1) [http://integrity.prous.com].

In this context searching for new selective and effective serotonin 5-HT$_6$ receptor antagonists seems to be original and perspective approach to the development of novel drug substances for treating of a great number of neurological and neurodegenerative diseases and cognitive disorders.

There are many publications in scientific literature describing various biologically active arylsulfonyl substituted azaheterocycles, among them serotonin receptor ligands. For example, substituted 1-(2-aminoethyl)-4-(arylsulfonyl)pyrazoles of general formula A1 were described as serotonin 5-HT$_{2c}$ receptor ligands [WO 2003057674 A1] and substituted 7-amino-3-(sulfonyl)pyrazolo[1,5-a]pyrimidines A2 as serotonin 5-HT$_6$ receptor antagonists [EP 941994 A1, 1999]

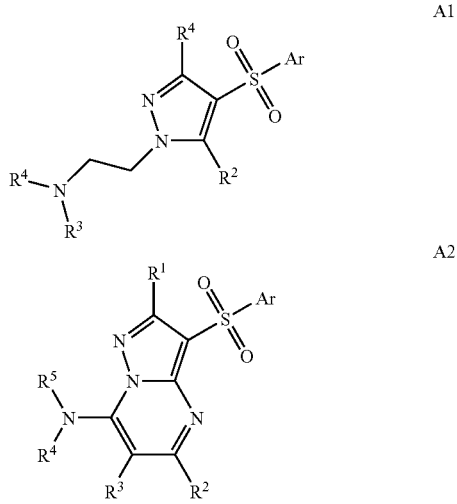

A1: Ar=alkyl, aryl; R$^1$ and R$^2$=H, OH, alkyl, alkoxy; R$^3$ and R$^4$=H, alkyl, aryl.
A2: Ar=aryl, heterocyclyl; R$^1$=H, alkyl, alkylthio; R$^2$=H, alkyl, halogen; R$^3$=H, alkyl, hydroxyalkyl; R$^4$ and R$^5$=H; NR$^4$R$^5$=piperazinyl.

With the aim of working out novel highly effective neuroprotective medicaments the authors of the invention carried out widespread investigation in the field of substituted 3-(sulfonyl)pyrazolo[1,5-a]pyrimidines, as a result of which novel drug substances which were 5-HT$_6$ receptor antagonists have been found.

DISCLOSURE OF THE INVENTION

In the context of the invention, the terms are generally defined as follows:
"Agonists" mean ligands being bound to receptors of definite type actively promote transferring their specific signal and by that cause the biological response of the cell.

"Azaheterocycle" means aromatic or nonaromatic mono- or polycyclic system with at least one nitrogen atom. Azaheterocycles may have one or more "cyclic system substituents".
"Alkyl" means aliphatic hydrocarbon straight or branched group with 1-12 carbon atoms. Branched means alkyl chain with one or more "lower alkyl" substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, a carboxy, alkynyloxy, aralkoxy, aryloxy, aryloxycarbonyl, alkylthio, heteroarylthio, aralkylthio, arylsulfonyl, alkylsulfonylheteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or R$_k^a$R$_{k+1}^a$N—, R$_k^a$R$_{k+1}^a$NC(=O)—, R$_k^a$R$_{k+1}^a$NC(=S)—, R$_k^a$R$_{k+1}^a$NSO$_2$—, where R$_k^a$ and R$_{k+1}^a$ independently of each other represent "amino group" substituent, the meanings thereof are defined in this section, for example, hydrogen, alkyl, aryl, aralkyl, heteroaralkyl, heterocyclyl or heteroaryl, or R$_k^a$ and R$_{k+1}^a$ together with the N-atom, they are attached to, form through R$_k^a$ and R$_{k+1}^a$ 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl and pyridylmethyloxycarbonylmethyl. The preferred "alkyl substituents" are cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or R$_k^a$R$_{k+1}^a$N—, R$_k^a$R$_{k+1}^a$NC(=O)—, annelated arylheterocyclenyl, annelated arylheterocyclyl.

"Alkyloxyalkyl" means alkyl-O-alkyl group wherein alkyl groups are independent of each other and defined in this section. Preferred alkyloxyalkyl groups are methoxyethyl, ethoxymethyl, n-butoxymethyl, methoxypropyl and iso-propyloxyethyl.

"Alkylthio or alkylsulfanyl" means alkyl-S— group wherein alkyl group is defined in this section.

"Alkoxy" means alkyl-O-group, wherein alkyl is defined in this section. The preferred alkoxy groups are methoxy, ethoxy, n-propoxy, iso-propoxy and n-butoxy.

"Antagonists" mean ligands being bound to definite receptors do not cause active cellular responses. Antagonists prevent binding between agonists and receptors and by that block specific receptor signal transmission.

"Aryl" means aromatic mono- or polycyclic system with 6-14 carbon atoms, mainly from 6 to 10 C-atoms. Aryl may have one or more "cyclic system substituents" of the same or different structure. Phenyl, substituted phenyl, naphthyl or substituted naphthyl are representatives of aryl groups. Aryl could be annelated with nonaromatic cyclic system or heterocycle.

"Arylsulfonyl" means aryl-SO$_2$-group, wherein the meaning of aryl is defined in this section.

"Halogen" means fluorine, chlorine, bromine and iodine. Preference is given to fluorine, chlorine and bromine.

"Heteroaryl" means aromatic mono- or polycyclic system with 5-14 carbon atoms, preferably from 5 to 10, wherein one or more carbon atoms are substituted by one or more heteroatoms, such as N, S or O. Prefix "aza", "oxa" or"thia" before "heteroaryl" means that N, O or S atoms are introduced in the appropriate cyclic fragment. N-Atom of heteroaryl Cycle could be oxidized to N-oxide. Heteroaryl may have one or more "cyclic system substituents" of the same or different structure. Pyrrolyl, furanyl, thienyl, pyridyl, pyrazinyl, pyrimidinyl, isoxazolyl, isothiazolyl, tetrazolyl, oxazolyl, thiazolyl, pyrazolyl, furazanyl, triazolyl, 1,2,4-thiadiazolyl, pyridazinyl, quinoxalinyl, phthalazinyl, imidazo[1,2-a]pyridinyl, imidazo[2,1-b]thiazolyl, benzofurazanyl, indolyl, azaindolyl, benzoimidazolyl, benzothiazenyl, quinolinyl, imidazolyl, thienopyridyl, quinazolinyl, thienopyrimidinyl, pyrrolopyridinyl, imidazopyridinyl, isoquinolinyl, benzoazaindolyl, 1,2,4-triazinyl, thienopyrrolyl, furopyrrolyl and others are the representatives of heteroaryl radicals.

"Heterocyclyl" means aromatic or nonaromatic saturated mono- or polycyclic system with 3-10 carbon atoms, preferably from 5 to 6 carbon atoms wherein one or more carbon atoms are substituted by heteroatom such as N, O or S. Prefix "aza", "oxa" or "thia" before "heterocyclyl" means, that N, O or S atoms are introduced in the appropriate cyclic fragment. Heterocyclyl may have one or more "cyclic system substituents" of the same or different structure. N— And S-atoms of the heterocyclic fragment could be oxidized to N-oxide, S-oxide and S-dioxide. Piperidinyl, pyrrolidinyl, piperazinyl, morpholinyl, thiomorpholinyl, thiazolidinyl, 1,4-dioxane-2-yl, tetrahydrofuranyl, tetrahydrothiophenyl and others are examples of heterocyclyl.

"Hydrate" means stoichiometric or nonstoichiometric compositions of the compounds or their salts with water.

"Hydroxyalkyl" means HO-alkyl-group wherein alkyl is defined in this section.

"Substituent" means chemical radical attached to scaffold (fragment), for example, "alkyl substituent", "amino group substituent", "carbamoyl substituent", and "cyclic system substituent", the meanings thereof are defined in this section.

"Drug substance" means physiologically active compound of synthetic or other (biotechnological, vegetable, animal, microbe and so on) origin exhibiting pharmacological activity and being an active ingredient of pharmaceutical composition employed in production and preparation of medicaments.

"Medicament"—is compound or mixture of compounds representing pharmaceutical composition in the form of tablets, capsules, injections, ointments and other finished pharma product intended for restoration, improvement or modification of physiological functions at humans and animals, and for treatment and prophylaxis of diseases; diagnostics, anesthesia, contraception, cosmetology and others.

"Ligands" (from Latin ligo) represent chemical compounds (small molecule, peptide, protein, inorganic ion, and so on) capable to interact with receptors which convert this interaction into specific signal.

"Lower alkyl" means straight or branched alkyl with 1-4 carbon atoms.

"Therapeutic kit" is simultaneously administered combination of two or more drug substances with different mechanism of pharmacological action and aimed at different biotargets taking part in pathogenesis of the disease.

"Pharmaceutical composition" means composition comprising, at least, one of compounds of general formula 1 and, at least, one of components selected from pharmaceutically acceptable and pharmacologically compatible fillers, solvents, diluents, auxiliary, distributing and sensing agents, delivery agents, such as preservatives, stabilizers, disintegrators, moisteners, emulsifiers, suspending agents, thickeners, sweeteners, flavoring agents, aromatizing agents, antibacterial agents, fungicides, lubricants, and prolonged delivery controllers, the choice and suitable proportions of which depend on the nature and way of administration and dosage.

Examples of suitable suspending agents are: ethoxylated isostearyl alcohol, polyoxyethene, sorbitol and sorbitol ether, microcrystalline•cellulose, aluminum metahydroxide, bentonite, agar-agar and tragacant and mixtures thereof as well. Protection against microorganism action can be provided by various antibacterial and antifungal agents, such as: parabens, chlorobutanol, sorbic acid, and similar compounds. Composition may also contain isotonic agents, such as: sugar, sodium chloride, and similar compounds. Prolonged effect of the composition may be achieved by agents slowing down absorption of the active ingredient, for example, aluminum monostearate and gelatin. Examples of suitable carriers, solvents, diluents and delivery agents include water, ethanol, polyalcohols and their mixtures, natural oils (such as olive oil) and injection-grade organic esters (such as ethyl oleate). Examples of fillers are: lactose, milk-sugar, sodium citrate, calcium carbonate, calcium phosphate and the like. Examples of disintegrators and distributors are starch, alginic acid and its salts, and silicates. Examples of suitable lubricants are: magnesium stearate, sodium lauryl sulfate, talc and polyethylene glycol of high molecular weight. Pharmaceutical composition for peroral, sublingual, transdermal, intramuscular, intravenous, subcutaneous, local or rectal administration of active ingredient, alone or in combination with another active compound may be administered to humans and animals in standard administration form, or in mixture with traditional pharmaceutical carriers. Suitable standard administration forms include peroral forms such as tablets, gelatin capsules, pills, powders, granules, chewing-gums and peroral solutions or suspensions, for example, therapeutic kit; sublingual and transbuccal administration forms; aerosols; implants; local, transdermal, subcutaneous, intramuscular, intravenous, intranasal or intraocular forms and rectal administration forms.

"Pharmaceutically acceptable salt" means relatively nontoxic both organic and inorganic salts of acids and bases disclosed in this invention. Salts could be prepared in situ during the process of synthesis, isolation or purification of compounds or they could be prepared as such. In particular, salts of bases could be prepared starting from purified bases disclosed in the invention and suitable organic or mineral acid. Examples of salts prepared in this manner include hydrochlorides, hydrobromides, sulfates, bisulfates, phosphates, nitrates, acetates, oxalates, valeriates, oleates, palmitates, stearates, laurates, borates, benzoates, lactates, p-toluenesulfonates, citrates, maleates, fumarates, succinates, tartrates, methane sulphonates, malonates, salicylates, propionates, ethane sulphonates, benzene sulfonates, sulfamates and the like (Detailed description of such salt properties is given in: Berge S. M., et al., "Pharmaceutical Salts" J. Pharm. Sci., 1977, 66: 1-19). Salts of disclosed acids may be prepared by reaction of purified acids specifically with suitable base; moreover, metal salts and amine salts may be synthesized too. Metal salts are salts of sodium, potassium, calcium, barium, magnesium, lithium and aluminum; sodium and potassium salts being preferred. Suitable inorganic bases from which metal salts can be prepared are: sodium hydroxide, carbonate, bicarbonate and hydride; potassium hydroxide, carbonate and bicarbonate, lithium hydroxide, calcium hydroxide, magnesium hydroxide, zinc hydroxide. Organic bases suitable for preparation of disclosed acid salts are amines and amino acids the basicity of which is sufficient enough to produce stable salt and suitable for use in medical purposes (in particular, they are to have low toxicity). Such amines include ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl)aminomethane and the like. Besides, salts can be prepared using some tetraalkylammonium hydroxides, such as holine, tetramethylammonium, tetraethylammonium, and the like. Amino acids may be selected from the main amino acids-lysine, ornithine and arginine.

The subject of the present invention is novel substituted 3-(arylsulfonyl)pyrazolo[1,5-a]pyrimidines of general formula 1 or pharmaceutically acceptable salts and/or hydrates thereof,

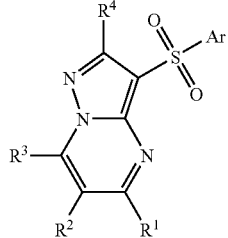

1 wherein:
Ar represents optionally substituted aryl or optionally substituted heterocyclyl;
$R^1$, $R^2$ and $R^3$ independently of each other represent hydrogen, $C_1$-$C_3$ alkyl or phenyl;
$R^4$ represents hydrogen, optionally substituted $C_1$-$C_5$ alkyl, substituted hydroxy group or substituted sulfanyl group.

The preferable compounds are substituted 5,7-dimethyl-3-(arylsulfonyl)pyrazolo[1,5-a]pyrimidines of general formula 1.1 or pharmaceutically acceptable salts and/or hydrates thereof,

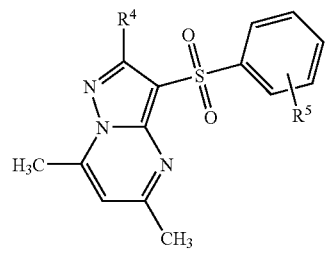

1.1 wherein:
$R^4$ is as defined above;
$R^5$ represents one or more optionally identical substituents selected from hydrogen, lower alkyl, trifluoromethyl, alkoxy group, substituted amino group or halogen.

The preferred compounds are 5,7-dimethyl-3-(phenylsulfonyl)pyrazolo[1,5-a]pyrimidine 1.1(1), 5,7-dimethyl-2-(2-hydroxyethyl)-3-(phenylsulfonyl)pyrazolo[1,5-a]pyrimidine 1.1(2), 5,7-dimethyl-3-(4-fluorophenylsulfonyl)pyrazolo[1,5-a]pyrimidine 1.1(3), 5,7-dimethyl-2-(2-hydroxyethyl)-3-(4-fluorophenylsulfonyl)pyrazolo[1,5-a]pyrimidine 1.1(4), 5,7-dimethyl-2-methylsulfanyl-3-(phenylsulfonyl)pyrazolo[1,5-a]pyrimidine 1.1(5), 5,7-dimethyl-2-ethylsulfanyl-3-(phenylsulfonyl)pyrazolo[1,5-a]pyrimidine 1.1(6), 5,7-dimethyl-2-methylsulfanyl-3-(4-fluorophenylsulfonyl)pyrazolo[1,5-a]pyrimidine 1.1(7), 5,7-dimethyl-2-ethylsulfanyl-3-(4-fluorophenylsulfonyl)pyrazolo[1,5-a]pyrimidine 1.1(8), 5,7-dimethyl-2-methylsulfanyl-3-(3-fluorophenylsulfonyl)pyrazolo[1,5-a]pyrimidine 1.1(9), 5,7-dimethyl-2-ethylsulfanyl-3-(3-fluorophenylsulfonyl)pyrazolo[1,5-a]pyrimidine 1.1(10), 5,7-dimethyl-2-methylsulfanyl-3-(3-chlorophenylsulfonyl)pyrazolo[1,5-a]pyrimidine 1.1(11), 5,7-dimethyl-2-ethylsulfanyl-3-(3-chlorophenylsulfonyl)pyrazolo[1,5-a]pyrimidine 1.1(12) or pharmaceutically acceptable salts and/or hydrates thereof,

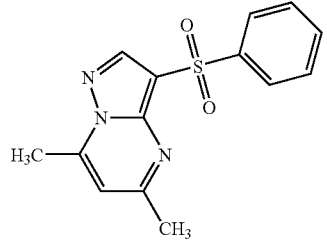 [SMILES: Cc1cc(C)n2ncc(S(=O)(=O)c3ccccc3)c2n1]

1.1(1)

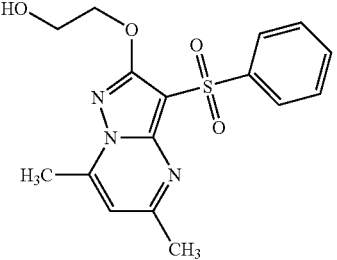 [SMILES: Cc1cc(C)n2nc(OCCO)c(S(=O)(=O)c3ccccc3)c2n1]

1.1(2)

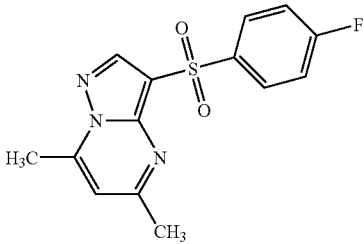

1.1(3)

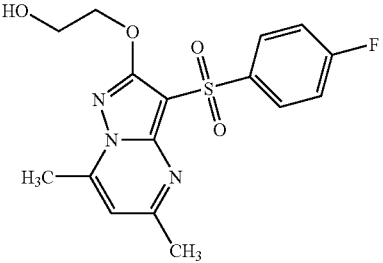 [SMILES: Cc1cc(C)n2nc(OCCO)c(S(=O)(=O)c3ccc(F)cc3)c2n1]

1.1(4)

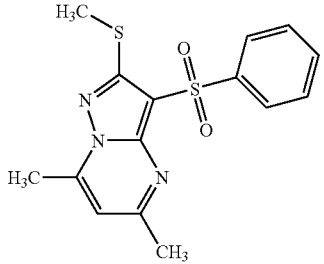 [SMILES: CSc1nn2c(C)cc(C)nc2c1S(=O)(=O)c1ccccc1]

1.1(5)

-continued 1.1(6)
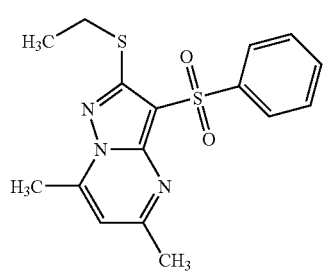 [SMILES: CCSc1nn2c(C)cc(C)nc2c1S(=O)(=O)c1ccccc1]

1.1(7)
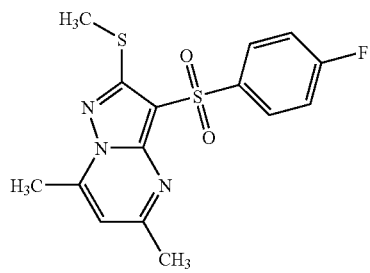 [SMILES: CSc1nn2c(C)cc(C)nc2c1S(=O)(=O)c1ccc(F)cc1]

1.1(8)
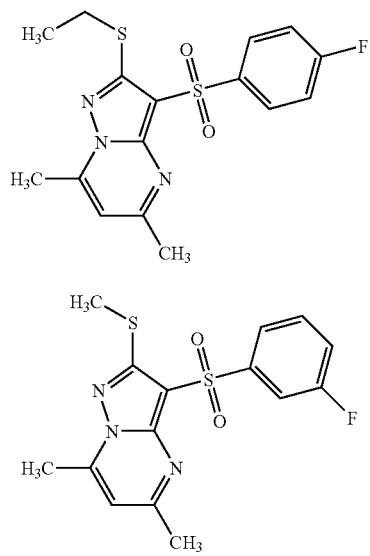

1.1(9)

1.1(10)
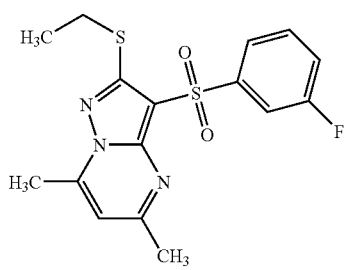 [SMILES: CCSc1nn2c(C)cc(C)nc2c1S(=O)(=O)c1cccc(F)c1]

1.1(11)
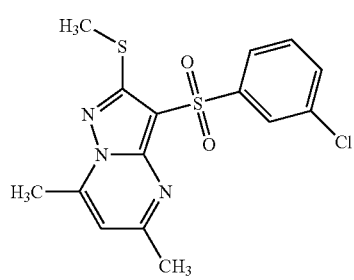 [SMILES: CSc1nn2c(C)cc(C)nc2c1S(=O)(=O)c1cccc(Cl)c1]

-continued 1.1(12)
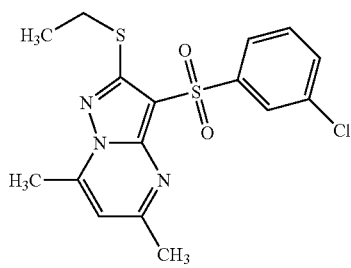 [SMILES: CCSc1nn2c(C)cc(C)nc2c1S(=O)(=O)c1cccc(Cl)c1]

The subject of the present invention is method for preparation of substituted 3-(arylsulfonyl)pyrazolo[1,5-a]pyrimidines of general formulas 1, 1.1 and compounds of formulas 1.1(1)-1.1(12) by interaction of 3-amino-4-arylsulfonyl-2H-pyrazoles of general formula 2 with corresponding β-dicarbonyl compounds of general formula 3 and subsequent isolation or separation of the reaction products (A, B) according to scheme given below.

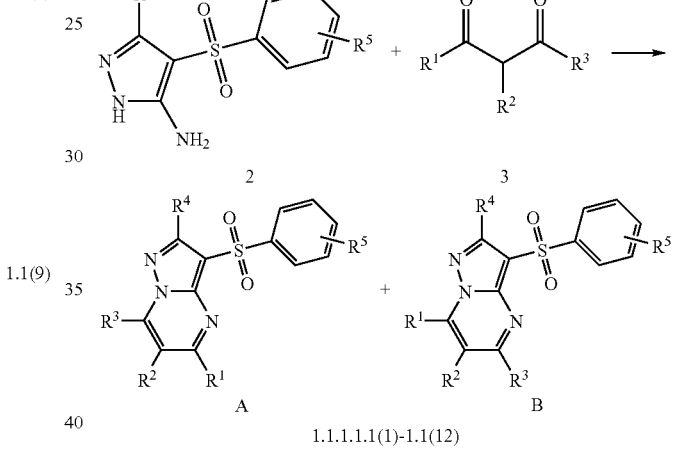

1.1.1.1.1(1)-1.1(12)

wherein:
$R^1$, $R^2$, $R^3$, $R^4$ and $R^5$ are all as defined above.

If diketones 3 are symmetrical compounds ($R^1=R^3$), only one product of the reaction could be obtained A=B. If the diketones used are unsymmetrical $R^1 \ne R^3$, mixture of two isomeric 3-(arylsulfonyl)pyrazolo[1,5-a]pyrimidines A and B are usually formed, which could be separated by recrystallization or preparative chromatography.

The subject of the present invention is also serotonin 5-HT$_6$ receptor antagonists which are compounds of general formulas 1, 1.1.

The subject of the present invention is drug substance for pharmaceutical compositions and medicaments which is, at least, one of antagonists of serotonin 5-HT$_6$ receptors of general formulas 1, 1.1, or compounds of formulas 1.1(1), 1.1(2), 1.1(3), 1.1(4), 1.1(5), 1.1(6), 1.1(7), 1.1(8), 1.1(9), 1.1(10), 1.1(11), 1.1(12).

The subject of the present invention is drug substance for pharmaceutical compositions and medicaments which is, at least, one of 3-(arylsulfonyl)pyrazolo[1,5-a]pyrimidines of general formulas 1, 1.1, or compounds of formulas 1.1(1), 1.1(2), 1.1(3), 1.1(4), 1.1(5), 1.1(6), 1.1(7), 1.1(8), 1.1(9), 1.1(10), 1.1(11), 1.1(12).

The subject of the present invention is pharmaceutical composition for prophylaxis and treatment of various conditions and diseases of CNS at humans and warm-blooded animals, comprising pharmaceutically effective amount of novel drug substance which is, at least, one of 3-(arylsulfonyl)pyrazolo[1,5-a]pyrimidines of general formulas 1, 1.1, or compounds of formulas 1.1(1), 1.1(2), 1.1(3), 1.1(4), 1.1(5), 1.1(6), 1.1(7), 1.1(8), 1.1(9), 1.1(10), 1.1(11), 1.1(12).

Pharmaceutical compositions may include pharmaceutically acceptable excipients. Pharmaceutically acceptable excipients mean diluents, auxiliary agents and/or carriers applied in the sphere of pharmaceutics. According to the invention pharmaceutical composition together with drug substance of general formula 1 may include other active ingredients provided that they do not give rise to undesirable effects, such as allergic reactions.

If needed, according to the present invention pharmaceutical compositions can be used in clinical practice in various forms prepared by mixing the said compositions with traditional pharmaceutical carries, for example, peroral forms (such as, tablets, gelatinous capsules, pills, solutions or suspensions); forms for injections (such as, solutions or suspensions for injections, or a dry powder for injections which requires only addition of water for injections before utilization); local forms (such as, ointments or solutions).

According to the present invention the carriers used in pharmaceutical compositions represent carriers which are used in the sphere of pharmaceutics for preparation of commonly used forms. Binding agents, greasing agents, disintegrators, solvents, diluents, stabilizers, suspending agents, colorless agents, taste flavors are used for peroral forms; antiseptic agents, solubilizers, stabilizers are used in forms for injections; base materials, diluents, greasing agents, antiseptic agents are used in local forms.

The subject of the present invention is also method for preparation of pharmaceutical composition by mixing a drug substance which is, at least, one of serotonin $5\text{-}HT_6$ receptor antagonist of general formulas 1, 1.1, or compounds of formulas 1.1(1), 1.1(2), 1.1(3), 1.1(4), 1.1(5), 1.1(6), 1.1(7), 1.1(8), 1.1(9), 1.1(10), 1.1(11), 1.1(12) with inert filler and/or solvent.

The subject of the present invention is also a medicament in the form of tablets, capsules, or injections, placed in pharmaceutically acceptable packing comprising a drug substance which is, at least, one of serotonin $5\text{-}HT_6$ receptor antagonists of general formulas 1, 1.1, or compounds of formulas 1.1(1), 1.1(2), 1.1(3), 1.1(4), 1.1(5), 1.1(6), 1.1(7), 1.1(8), 1.1(9), 1.1(10), 1.1(11), 1.1(12) or pharmaceutical composition including this drug substance, intended for treatment and prophylaxis of pathological states and CNS diseases pathogenesis of which is associated with disturbance of serotonin $5\text{-}HT_6$ receptor activation.

According to the invention preferable medicament is a medicament for treatment and prophylaxis of AD and Huntington's disease.

According to the invention preferable medicament is a medicament for treatment and prophylaxis of psychotic disorders and schizophrenia.

According to the invention the preferable medicament is medicament for treatment and prophylaxis of obesity.

The subject of the present invention is a therapeutic kit for prophylaxis and treatment of various diseases pathogenesis of which is associated with serotonin $5\text{-}HT_6$ receptors at humans and animals, including a novel medicament comprising a drug substance of general formulas 1, 1.1, 1.1(1), 1.1(2), 1.1(3), 1.1(4), 1.1(5), 1.1(6), 1.1(7), 1.1(8), 1.1(9), 1-0.1(10), 1.1(11), 1.1(12).

According to the invention preferable therapeutic kit is a therapeutic kit for prophylaxis and treatment of neurological disorders, neurodegenerative and cognitive diseases at humans and animals including a novel medicament which comprises a drug substance of general formulas 1, 1.1, 1.1(1), 1.1(2), 1.1(3), 1.1(4), 1.1(5), 1.1(6), 1.1(7), 1.1(8), 1.1(9), 1.1(10), 1.1(11), 1.1(12).

According to the invention preferable therapeutic kit is a therapeutic kit for prophylaxis and treatment of AD, Huntington's disease, psychotic disorders, schizophrenia, hypoxia-ischemia, hypoglycemia, convulsive states, brain injuries, lathyrism, amyotrophic lateral sclerosis, obesity or insult, including a novel medicament, which comprises a drug substance of general formulas 1, 1.1, 1.1(1), 1.1(2), 1.1(3), 1.1(4), 1.1(5), 1.1(6), 1.1(7), 1.1(8), 1.1(9), 1.1(10), 1.1(11), 1.1(12).

Therapeutic kits for prophylaxis and treatment of various diseases pathogenesis of which is associated with serotonin $5\text{-}HT_6$ receptors at humans and animals, among them neurological disorders, neurodegenerative and cognitive diseases of animals and humans, AD, Huntington's disease, psychotic disorders, schizophrenia, hypoxia-ischemia, hypoglycemia, convulsive states, brain injuries, lathyrism, amyotrophic lateral sclerosis, obesity or insult, along with drug substances disclosed in the invention, may include other active ingredients such as: nonsteroidal anti-inflammatory drugs (Orthophene, Indomethacin, Ibuprophen and others); acetylcholinesterase inhibitors (Tacrine, Amiridine, Fizostigmine, Aricept, Phenserine and others); estrogens (for example, Estradiol); NMDA-receptor antagonists (for example, Memantine, Neramexane); nootropic drugs (for example, Pyracetam, Fenibut and others); AMPA receptor modulators (for example, Ampalex); antagonists of cannabinoid receptors CB-1 (for example, Rimonabant); monoaminooxidase inhibitors MAO-B and/or MAO-A (for example, Rasagiline); antiamyloidogenic drugs (for example, Tramiprosate); lowering β-amyloide neurotoxicity compounds (for example, Indole-3-propionic acid); γ- and/or β-secretase inhibitors; M1-muscarinic receptor agonists (for example, Cevimeline); metal helates (for example, Clioquinol); GABA(A) receptor antagonists (for example, CGP-36742); monoclonal antibodies (for example, Bapineuzumab); antioxidants; neurotrophic agents (for example, Cerebrolisine); antidepressants (for example, Imipramine, Sertraline and so on) and others.

According to the invention preferable therapeutic kit is a therapeutic kit for overweight lowering and obesity treatment. The therapeutic kit for overweight lowering and obesity treatment along with drug substances disclosed in the invention, may include other active ingredients such as: anorectic drugs (for example, Fepranon, Desopimon, Masindole), hormone drugs (for example, Tircoidine), hypolipidemic means such as fibrates (for example, Fenofibrate), statines (for example, Lovastatine, Simvastatine, Pravastatine and Probucol), and also hypoglycemic drugs (sulfonylurea—for example, Butamide, Glibenclamide; biguanidines—for example, Buformine, Metamorphine) and drugs with some other mechanism of action, such as cannabinoid CB-1 receptor antagonists (Rimonabant), inhibitors of norepinephrine and serotonin reuptake (Sibutramine), inhibitors of ferments of fatty acids synthesis (Orlistat) and others, along with antioxidants, food additives and others.

The subject of the present invention is also a method for prophylaxis and treatment of various diseases, pathogenesis of which is associated with serotonin $5\text{-}HT_6$ receptors at humans and animals, among them neurological disorders, neurodegenerative and cognitive diseases, by introduction to the said mammals of novel medicament or novel therapeutic kit comprising a drug substance of general formulas 1, 1.1, 1.1(1), 1.1(2), 1.1(3), 1.1(4), 1.1(5), 1.1(6), 1.1(7), 1.1(8), 1.1(9), 1.1(10), 1.1(11), 1.1(12).

Medicaments could be introduced peroral or parenterally (for example, intravenously, subcutaneously, intraperitoneally or locally). Clinical dose of pharmaceutical composition or medicament comprising a drug substance of general formulas 1, 1.1, 1.1(1), 1.1(2), 1.1(3), 1.1(4), 1.1(5), 1.1(6), 1.1(7), 1.1(8), 1.1(9), 1.1(10), 1.1(11), 1.1(12), might be corrected depending on: therapeutic efficiency and bio-accessibility of active ingredients in patients' organism, rate of their exchange and removal from organism, and age, gender, and severity of patient's symptoms. Thus, the daily intake for adults normally being 10~500 mg, preferably 50~300 mg. Accordingly the above effective doses are to be taken into consideration while preparing medicaments of the present invention, each dose unit of the medicament contains 10~500 mg of a drug substance of general formulas 1, 1.1, 1.1(1), 1.1(2), 1.1(3), 1.1(4), 1.1(5), 1.1(6), 1.1(7), 1.1(8), 1.1(9), 1.1(10), 1.1(11), 1.1(12), preferably 50~300 mg. Following the instructions of physician or pharmacist, medicaments could be taken several times over specified periods of time (preferably, from one to six times).

Synthesis of serotonin 5-HT$_6$ receptor antagonists of general formula 1 and biological tests thereof are presented in examples given below. Analysis results of serotonin 5-HT$_6$ receptor antagonists of general formula 1 and their biological activity towards serotonin receptors are shown in Tables 2-4.

Starting reagents for synthesis of pyrazoles of general formulas 2A, 2B, 2C and 2D are sulfonylacetonitriles of general formula 2.1 which according to the schemes given below are transformed into 2-sulfonyl-acrylonitriles 2.2, the latter are turned into required final compounds by the action of hydrazine 2.3, as it was described in [EP 0941994 A1 (1999)].

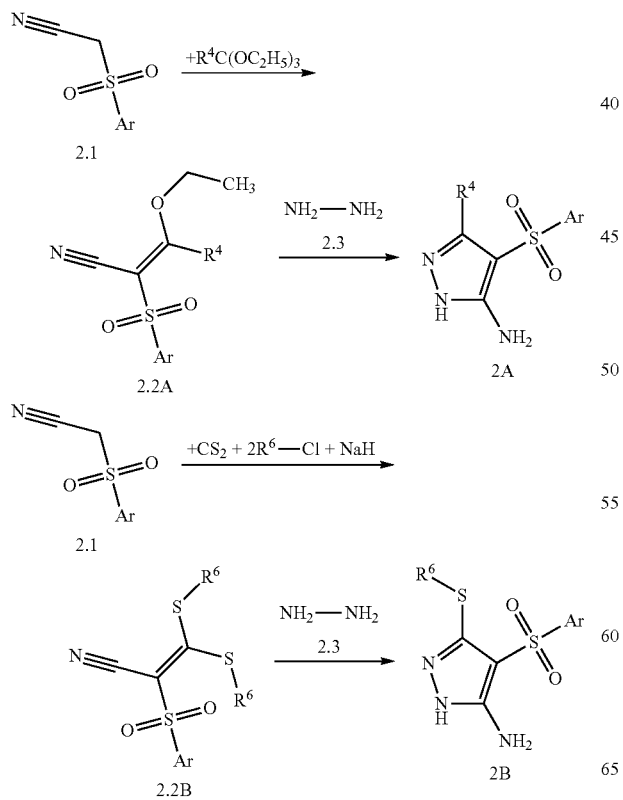

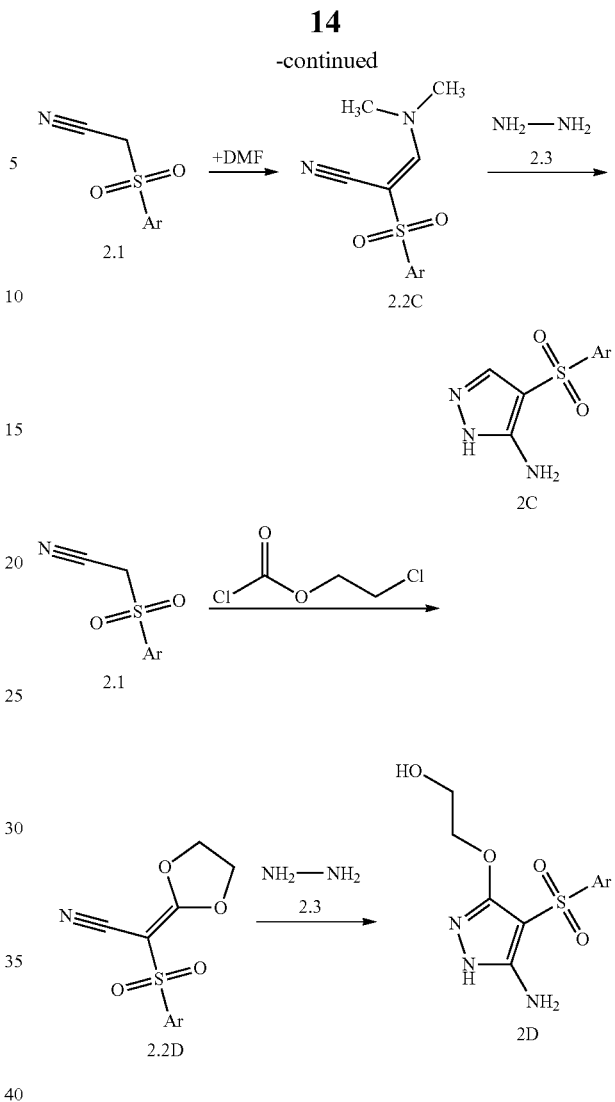

wherein: $R^4$ and Ar are all as defined above, $R^6$ represents lower alkyl.

BEST EMBODIMENT OF THE INVENTION

Below the invention is described by means of specific examples, which illustrate but not limit the scope of the invention.

Example 1

General method for preparation of substituted 3-sulfonylpyrazoles of general formulas 1, 1.1. Mixture of 0.005 mol of aminopyrazole 2 and 0.0055 mol of corresponding diketone 3 in 5 ml of acetic acid was boiled for 4 hours. After cooling the solid precipitated was filtered off, washed with methanol and water. If necessary, the product was subjected to recrystallization from proper solvent, or chromatographic purification or chromatographic separation. Yield of 3-(sulfonyl)pyrazolo[1,5-a]pyrimidines of general formulas 1, 1.1 was from 30% to 85%. Some examples of novel 3-(sulfonyl)pyrazolo[1,5-a]pyrimidines of general formula 1, their LCMS analysis, NMR data and % inhibition of 5-HT$_6$ receptors are presented in Table 2.

TABLE 2

5,7-Dimethyl 3-(arylsulfonyl)pyrazolo[1,5-a]pyrimidines of general formulas 1, 1.1 and % inhibition of 5-HT$_6$ receptors (I, %) by their 10 μM solutions.

| No | Formula | Mol. w. | LCMS m/z (M + 1) | NMR spectra | I, % |
|---|---|---|---|---|---|
| 1(1) | | 395.51 | 396 | | 88 |
| 1(2) | | 302.36 | 303 | | 77 |
| 1(3) | | 302.36 | 303 | | 78 |
| 1(4) | | 307.40 | 308 | | 69 |
| 1(5) | | 395.51 | 396 | | 68 |

TABLE 2-continued 5,7-Dimethyl 3-(arylsulfonyl)pyrazolo[1,5-a]pyrimidines of general formulas 1, 1.1 and % inhibition of 5-HT$_6$ receptors (I, %) by their 10 μM solutions.

| No | Formula | Mol. w. | LCMS m/z (M + 1) | NMR spectra | I, % |
|---|---|---|---|---|---|
| 1.1(1) | | 287.34 | 288 | $^1$H NMR (DMSO-D$_6$): 8.60 (s, 1 H); 8.02-8.06 (m, 2 H); 7.53-7.63 (m, 3 H); 7.18 (qv, J = 1 Hz, 1 H); 2.66 (d, J = 1 Hz, 3 H); 2.57 (s, 3 H). | 78 |
| 1.1(2) | | 347.40 | 348 | $^1$H NMR (DMSO-D$_6$): 7.97-8.01 (m, 2 H); 7.50-7.61 (m, 3 H); 7.05 (s, 1 H); 4.91 (t, J = 5.3 Hz, 1 H, exch. with D2O); 4.36 (t, J = 5.3 Hz, 2 H); 3.74 (qv, J = 5.3 Hz, 2 H); 2.55 (s, 3 H); 2.52 (s, 3 H). | 82 |
| 1.1(4) | | 365.39 | 366 | | 73 |
| 1.1(5) | | 333.43 | 334 | $^1$H NMR (CDCl$_3$, 400 MHz) δ 8.21-8.23 (m, 2 H), 7.45-7.54 (m, 3 H), 6.67 (s, 1 H), 2.68 (s, 3 H), 2.64 (s, 3 H), 2.62 (s, 3 H). | 104 |
| 1.1(6) | | 347.46 | 348 | | 104 |

TABLE 2-continued 5,7-Dimethyl 3-(arylsulfonyl)pyrazolo[1,5-a]pyrimidines of general formulas 1, 1.1 and % inhibition of 5-HT$_6$ receptors (I, %) by their 10 μM solutions.

| No | Formula | Mol. w. | LCMS m/z (M + 1) | NMR spectra | I, % |
|---|---|---|---|---|---|
| 1.1(7) | | 351.42 | 352 | (CDCl$_3$, 400 MHz) δ 8.23 (m, 2 H), 7.13 (t, J = 4.6 Hz, 3 H), 6.69 (s, 1 H), 2.69 (s, 3 H), 2.64 (s, 3 H), 2.62 (s, 3 H). | 101 |
| 1.1(8) | | 365.45 | 366 | | 102 |
| 1.1(9) | | 351.42 | 352 | $^1$H NMR (CDCl$_3$, 400 MHz) δ 8.00 (d, J = 8.0 Hz, 1 H), 7.96 (dt, J$_1$ = 8.0 Hz, J$_2$ = 2.0 Hz, 1 H), 7.45 (td, J$_1$ = 8.0 Hz, J$_2$ = 5.2 Hz, 1 H), 7.21 (tdd, J$_1$ = 8.4 Hz, J$_2$ = 2.4 Hz, J$_3$ = 0.4 Hz, 1 H), 6.70 (s, 1 H), 2.70 (s, 3 H), 2.66 (s, 3 H), 2.63 (s, 3 H). | 100 |
| 1.1(10) | | 365.45 | 366 | | 103 |
| 1.1(11) | | 367.88 | 368 | $^1$H NMR (DMCO-D$_6$, 400 MHz): δ 8.26 (m, 1 H), 8.09 (d, J = 7.6 Hz, 1 H), 7.48 (m, 1 H), 7.41 (t, J = 7.6 Hz, 1 H), 6.70 (s, 1 H), 2.70 (s, 3 H), 2.66 (s, 3 H), 2.63 (s, 3 H). | 101 |

TABLE 2-continued 5,7-Dimethyl 3-(arylsulfonyl)pyrazolo[1,5-a]pyrimidines of general formulas 1, 1.1 and % inhibition of 5-HT$_6$ receptors (I, %) by their 10 μM solutions.

| No | Formula | Mol. w. | LCMS m/z (M + 1) | NMR spectra | I, % |
|---|---|---|---|---|---|
| 1.1(12) | | 381.91 | 382 | | 101 |
| 1.1(13) | | 301.37 | 302 | $^1$H NMR (DMSO-D$_6$): 8.00-8.04 (m, 2 H); 7.52-7.62 (m, 3 H); 7.10 (s, 1 H); 2.62 (s, 3 H); 2.61 (s, 3 H); 2.55 (s 3 H). | 86 |
| 1.1(14) | | 319.36 | 320 | | 88 |
| 1.1(15) | | 361.49 | 362 | | 99 |
| 1.1(16) | | 367.88 | 368 | | 94 |

TABLE 2-continued 5,7-Dimethyl 3-(arylsulfonyl)pyrazolo[1,5-a]pyrimidines of general formulas 1, 1.1 and % inhibition of 5-HT$_6$ receptors (I, %) by their 10 μM solutions.

| No | Formula | Mol. w. | LCMS m/z (M + 1) | NMR spectra | I, % |
|---|---|---|---|---|---|
| 1.1(17) | | 363.46 | 364 | | 65.4 |
| 1.1(18) | | 377.49 | 378 | | 60.99 |
| 1.1(19) | | 376.50 | 377 | | 87 |
| 1.1(20) | | 385.87 | 387 | $^1$H NMR (CDCl$_3$, 400 MHz): δ 8.35 (dd, J$_1$ = 6.8 Hz, J$_2$ = 2.0 Hz, 1 H), 8.11 (dd, J$_1$ = 6.8 Hz, J$_2$ = 4.4 Hz, J$_3$ = 2.0 Hz, 1 H), 7.22 (t, J = 8.8 Hz, 1 H), 6.71 (d, J = 0.8 Hz, 1 H), 2.71 (d, J = 0.8 Hz, 3 H), 2.66 (s, 3 H), 2.63 (s, 3 H). | 100 |

TABLE 2-continued 5,7-Dimethyl 3-(arylsulfonyl)pyrazolo[1,5-a]pyrimidines of general formulas 1, 1.1 and % inhibition of 5-HT$_6$ receptors (I, %) by their 10 μM solutions.

| No | Formula | Mol. w. | LCMS m/z (M + 1) | NMR spectra | I, % |
|---|---|---|---|---|---|
| 1.1(21) | [structure] | 355.82 | 320 | | 78 |
| 1.1(22) | [structure] | 374.47 | 375 | | 66 |

Example 2

Determination of antagonistic activity of compounds of general formula 1 towards 5-HT$_6$ receptors. Compounds of general formula 1 were tested for their ability to prevent 5-HT$_6$ receptor activation by serotonin. HEK 293 cells (cells of human embryo's kidney) with artificially expressed 5-HT$_6$ receptor, activation of which by serotonin leads to increasing the concentration of intracellular cAMP were used. The content of intracellular cAMP was determined using reagent kit LANCE cAMP (PerkinElmer) according to the method described by the manufacturer of the kit [http://las.perkinelmer.com/content/Manuals/MAN_LANCEcAMP384KitUser.pdf].

Effectiveness of compounds was estimated by their ability to reduce the content of intracellular cAMP induced by serotonin.

Table 2 presents data on % inhibition of 5-HT$_6$ receptors by 10 μM solutions of compounds of general formula 1. As can be seen from the data given, tested compounds show observable activity towards serotonin 5-HT$_6$ receptors.

Table 3 shows concentration dependence of inhibition of intracellular cAMP production stimulated by serotonin by some drug substances of general formula 1 testifying antagonistic activity thereof, and IC$_{50}$ values testifying their moderate or high activity in the setting of functional assay.

TABLE 3

Concentration dependence of serotonin 5-HT$_6$ receptors inhibition by substances of general formula 1 and IC$_{50}$ values in the setting of functional assay.

| No | Formula | IC$_{50}$, μM |
|---|---|---|
| 1.1(1) | [structure] | >1.0 |
| 1.1(5) | [structure] | 0.030 |

TABLE 3-continued

Concentration dependence of serotonin 5-HT$_6$ receptors inhibition by substances of general formula 1 and IC$_{50}$ values in the setting of functional assay.

| No | Formula | IC$_{50}$, μM |
|---|---|---|
| 1.1(6) | (structure) | 0.050 |
| 1.1(7) | (structure) | 0.112 |
| 1.1(9) | (structure) | 0.025 |
| 1.1(11) | (structure) | 0.020 |
| 1.1(15) | (structure) | 0.080 |
| 1.1(16) | (structure) | 0.230 |
| 1.1(17) | (structure) | 0.440 |
| 1.1(18) | (structure) | 0.320 |
| 1.1(20) | (structure) | 0.046 |

Example 3

Determination of activity of serotonin 5-HT$_6$ receptor antagonists of the general formula 1 in the setting of competitive binding to serotonin 5-HT$_6$ receptors.

Screening of disclosed compounds for their potential ability to interact with serotonin 5-HT$_6$ receptor was carried out by method of radioligand binding. For this purpose membrane species were prepared from expressing recombinant human 5-HT$_6$ receptor HeLa cells by means of their homogenization in glass homogenizer with subsequent separation of plasmatic membranes from cell nuclei, mitochondria's and cell wreckages by differential centrifugation. Determination of tested compounds binding to $5\text{-}HT_6$ receptors was carried out according to the method described in [Monsma F J Jr, Shen Y, Ward R P, Hamblin M W and Sibley D R, Cloning and expression of a novel serotonin receptor with high affinity for tricyclic psychotropic drugs. Mol. Pharmacol. 43:320-327, 1993]. In the preferable embodiment membrane preparations were incubated with radioligand (1.5 nM [$^3$H] Lysergic acid diethylamide) without and in the presence of investigated compounds for 120 min at 37° C. in medium consisting of mM Tris-HCl, pH 7.4, 150 mM NaCl, 2 mM Ascorbic Acid, 0.001% BSA. After incubation the samples were filtered in vacuo on glass-microfiber filters G/F (Millipor, USA), filters were washed three times with cold solution of medium and radioactivity was measured by scintillation counter Micro-Beta 340 (PerkinElmer, USA). Nonspecific binding which made up 30% of overall binding was determined by incubation of membrane preparations with radioligand in the presence of 5 μM Serotonin (5-HT). Methiothepin was used as positive control. Binding of tested compounds to the receptor was determined by their ability to displace the radioligand and expressed in percent of displacement. The percent of displacement was calculated according to the following equation:

$$\% \, I = \frac{TA - CA}{TA - NA} * 100,$$

wherein: TA—was overall radioactivity in the presence of radioligand only, CA—was radioactivity in the presence of radioligand and tested compound and NA—was radioactivity in the presence of radioligand and Serotonin (5 μM).

Table 4 presents the test results for some 3-(arylsulfonyl) pyrazolo[1,5-a]pyrimidines of general formula 1 and Methiothepin (control compound), which testify the high activity of drug substances of general formula 1 towards serotonin $5\text{-}HT_6$ receptors.

TABLE 4

Concentration dependences of serotonin $5\text{-}HT_6$ receptors inhibition by drug substances of general formula 1 and $IC_{50}$ values in the setting of competitive binding

| No | Substance | $IC_{50}$, nM | $K_i$, nM |
|---|---|---|---|
| Control | Methiothepin | 1.3 | 0.603 |
| 1.1(1) | 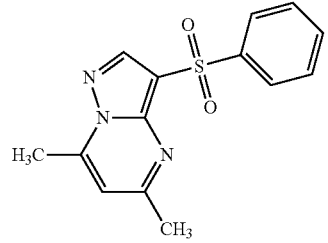 [SMILES: Cc1cc(C)n2ncc(S(=O)(=O)c3ccccc3)c2n1] | 510 | 237 |
| 1.1(2) | 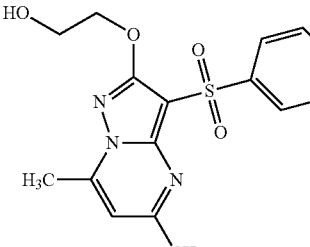 | 477 | 222 |
| 1.1(5) | 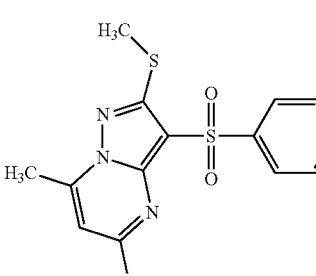 | 4.61 | 2.14 |

TABLE 4-continued

Concentration dependences of serotonin 5-HT$_6$ receptors inhibition by drug substances of general formula 1 and IC$_{50}$ values in the setting of competitive binding

| No | Substance | IC$_{50}$, nM | K$_i$, nM |
|---|---|---|---|
| 1.1(7) | | <10 | |
| 1.1(13) | | 147 | 68.4 |

Example 4

Preparation of medicaments in form of tablets. 1600 mg of starch, 1600 mg of ground lactose, 400 mg of talk and 1000 mg of 5,7-dimethyl-2-methylsulfanyl-3-(phenylsulfonyl)pyrazolo[1,5-a]pyrimidine 1.1(5) were mixed together and pressed into bar. The resultant bar was comminuted into granules and sifted through sieve to collect granules of 14-16 mesh. The granules thus obtained were shaped into tablets of suitable form weighing 560 mg each. According to the invention medicaments comprising other compounds of general formula 1 as drug substance could be prepared by the same procedure.

Example 5

Preparation of medicament in form of capsules. 5,7-dimethyl-2-methylsulfanyl-3-(phenylsulfonyl)pyrazolo[1,5-a]pyrimidine 1.1(5) and lactose powder were carefully mixed in ratio 2:1. The resultant powdery mixture was packed into gelatin capsules of suitable size by 300 mg to capsule.

Example 6

Preparation of medicament in form of compositions for intramuscular, intraperitoneal or hypodermic injections. 500 mg of 5,7-dimethyl-2-methylsulfanyl-3-(phenylsulfonyl)pyrazolo[1,5-a]pyrimidine 1.1(5), 300 mg of chlorobutanol, 2 ml of propylene glycol, and 100 ml of injectable water were mixed together. The resultant solution was filtered and placed into 1 ml ampoules, which were sealed and sterilized in autoclave.

INDUSTRIAL APPLICABILITY

The invention could be use in medicine, veterinary, biochemistry.

The invention claimed is:
1. A substituted 3-(arylsulfonyl)pyrazolo[1,5-a]pyrimidine compound of general formula 1, or a pharmaceutically acceptable salt thereof,

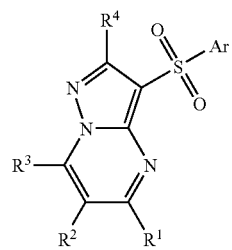

wherein:
Ar is an optionally substituted aryl;
R$^1$, R$^2$ and R$^3$ independently of each other represent hydrogen, C$_1$-C$_3$ alkyl or phenyl;
R$^4$ is a substituted hydroxy group or a substituted sulfanyl group; with the exception of:
5,7-dimethyl-3-(phenylsulfonyl)pyrazolo[1,5-a]pyrimidine;
5,7-dimethyl-3-tosylpyrazolo[1,5-a]pyrimidine;
5-methyl-3-(phenylsulfonyl)pyrazolo[1,5-a]pyrimidine;
3-(1H-1,2,4-triazol-3-ylsulfonyl)-2,5,7-trimethylpyrazolo[1,5-a]pyrimidine;
3-(1H-1,2,4-triazol-3-ylsulfonyl)-2-methoxy-5,7-dimethylpyrazolo[1,5-a]pyrimidine;
3-(1H-1,2,4-triazol-3-ylsulfonyl)-5,7-dimethylpyrazolo[1,5-a]pyrimidine;
3-(1H-1,2,4-triazol-3-ylsulfonyl)pyrazolo[1,5-a]pyrimidine;

N,N-diethyl-3-(2-methylpyrazolo[1,5-a]pyrimidin-3-yl-sulfonyl)-1H-1,2,4-triazol-1-carboxamid;

3-(2,5-dimethylpyrazolo[1,5-a]pyrimidin-3-ylsulfonyl)-N,N-diethyl-1H-1,2,4-triazol-1-carboxamid;

N,N-diethyl-3-(pyrazolo[1,5-a]pyrimidin-3-ylsulfonyl)-1H-1,2,4-triazol-1-carboxamid;

N,N-diethyl-3-(2,5,7-trimethylpyrazolo[1,5-a]pyrimidin-3-ylsulfonyl)-1H-1,2,4-triazol-1-carboxamid;

N,N-diethyl-3-(2-methoxy-5,7-dimethylpyrazolo[1,5-a]pyrimidin-3-ylsulfonyl)-1H-1,2,4-triazol-1-carboxamid;

5,7-dimethyl-3-[(4-methylpiperazin-1-yl)sulfonyl]pyrazolo[1,5-a]pyrimidine.

2. The compound of claim 1, of general formula 1.1, or a pharmaceutically acceptable salt thereof,

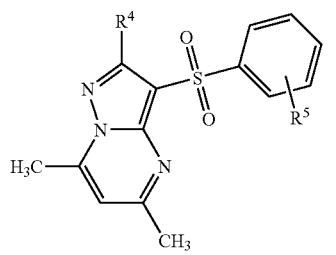

1.1 wherein: $R^4$ is as defined above; $R^5$ is one or two optionally identical substituents selected from hydrogen, lower alkyl, trifluoromethyl, alkoxy group, substituted amino group or halogen.

3. The compound of claim 2, selected from the group, consisting of 5,7-dimethyl-2-(2-hydroxyethyl)-3-(phenylsulfonyl)pyrazolo[1,5-a]pyrimidine 1.1(2), 5,7-dimethyl-2-(2-hydroxyethyl)-3-(4-fluorophenylsulfonyl)pyrazolo[1,5-a]pyrimidine 1.1(4), 5,7-dimethyl-2-methylsulfanyl-3-(phenylsulphonyl)pyrazolo[1,5-a]pyrimidine 1.1(5), 5,7-dimethyl-3-(phenylsulfonyl)-2-ethylsulfanyl-pyrazolo[1,5-a]pyrimidine 1.1(6), 5,7-dimethyl-2-methylsulfanyl-3-(4-fluorophenylsulfonyl)pyrazolo[1,5-a]pyrimidine 1.1(7), 5,7-dimethyl-2-ethylsulfanyl-3-(4-fluorophenylsulfonyl)pyrazolo[1,5-a]pyrimidine 1.1(8); 5,7-dimethyl-2-methylsulfanyl-3-(3-fluorophenylsulfonyl)pyrazolo[1,5-a]pyrimidine 1.1(9), 5,7-dimethyl-2-ethylsulfanyl-3-(3-fluorophenylsulfonyl)pyrazolo[1,5-a]pyrimidine 1.1(10), 5,7-dimethyl-2-methylsulfanyl-3-(3-chlorophenylsulfonyl)pyrazolo[1,5-a]pyrimidine 1.1(11), and 5,7-dimethyl-2-ethylsulfanyl-3-(3-chlorophenylsulfonyl)pyrazolo[1,5-a]pyrimidine 1.1(12), or a pharmaceutically acceptable salt thereof,

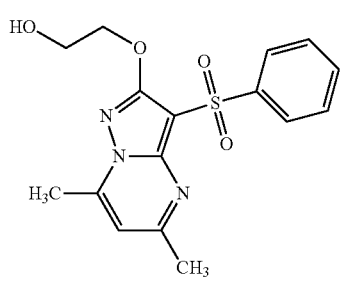

1.1(2)

-continued

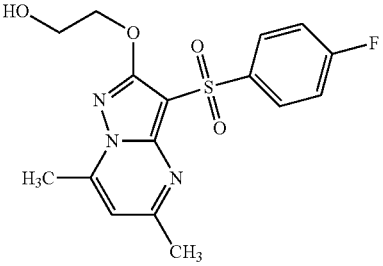

1.1(4)

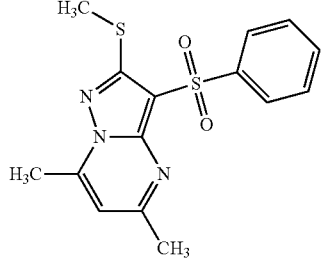

1.1(5)

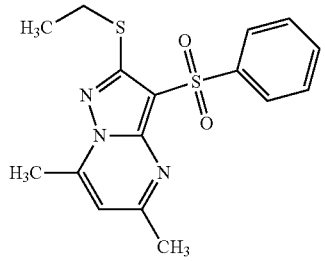

1.1(6)

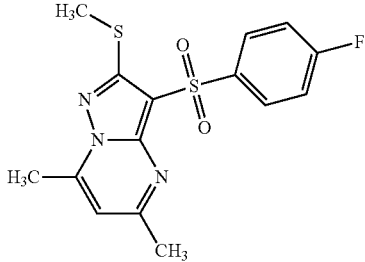

1.1(7)

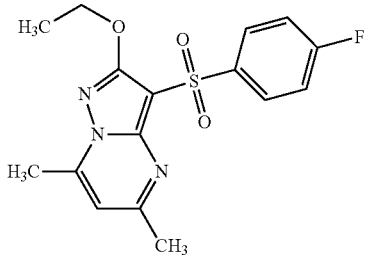

1.1(8)

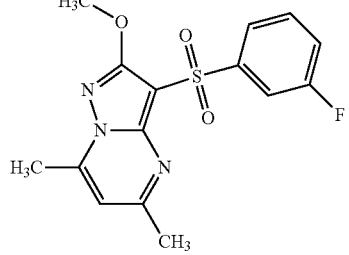

1.1(9)

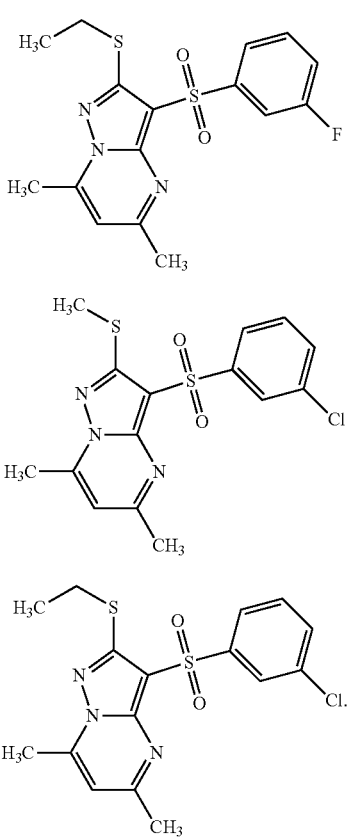

4. An antagonist of serotonin 5-HT$_6$ receptor comprising a compound of general formula 1 as claimed in any of claims 1-3.

5. A drug substance for pharmaceutical compositions and medicaments, comprising at least one compound of general formula 1 as claimed in any of claims 1-3.

6. A pharmaceutical composition comprising a pharmaceutically effective amount of a drug substance as claimed in claim 5 and an excipient or an inert filler, or a diluent.

7. A medicament in the form of a tablet, a capsule, or an injection placed in a pharmaceutically acceptable packing comprising a drug substance as claimed in claim 5 or a pharmaceutical composition as claimed in claim 6 for treating a pathological state or CNS disease pathogenesis of which is associated with disturbance of serotonin 5-HT$_6$ receptor activation.

8. A therapeutic kit for the treatment of various diseases, pathogenesis of which is associated with serotonin 5-HT$_6$ receptors in human and animal, comprising a drug substance as claimed in claim 5, or a pharmaceutical composition as claimed in claim 6, or a medicament as claimed in claim 7.

9. A therapeutic kit for the treatment of neurological disorders, neurodegenerative and cognitive diseases in human and animal, comprising a drug substance as claimed in claim 5, or pharmaceutical composition as claimed in claim 6, or medicament as claimed in claim 7.

10. A therapeutic kit for the treatment of Alzheimer's disease, Huntington's disease, psychic disorders, schizophrenia, hypoxia-ischemia, hypoglycemia, convulsive states, brain injuries, lathyrism, amyotrophic lateral sclerosis, obesity or insult in human and animal, comprising a drug substance as claimed in claim 5, or pharmaceutical composition as claimed in claim 6, or medicament as claimed in claim 7.

\* \* \* \* \*